US00PP23971P2

(12) United States Plant Patent
Mukundan

(10) Patent No.: US PP23,971 P2
(45) Date of Patent: Oct. 8, 2013

(54) ***AGLAONEMA* PLANT NAMED 'MUKGRES'**

(50) Latin Name: *Aglaonema hybrida*
Varietal Denomination: Mukgres

(75) Inventor: Parthasarathy Mukundan, Alwarpet Chennai (IN)

(73) Assignee: K.S.G.'s Farm & Nursery, Chennai (IN)

( * ) Notice: Subject to any disclaimer, the term of this patent is extended or adjusted under 35 U.S.C. 154(b) by 105 days.

(21) Appl. No.: 13/373,837

(22) Filed: Dec. 1, 2011

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — June Hwu
(74) *Attorney, Agent, or Firm* — C. A. Whealy

(57) ABSTRACT

A new and distinct cultivar of *Aglaonema* plant named 'Mukgres', characterized by its upright and outwardly arching plant habit; freely clumping habit; vigorous growth habit; relatively short internodes giving a compact, dense and full plant form; lanceolate leaves with dark green-colored midveins, margins and irregular chevrons alternating with contrasting greyed green-colored irregular chevrons; dark green-colored petioles; and relative tolerance to low temperatures.

3 Drawing Sheets

Botanical designation: *Aglaonema hybrida.*
Cultivar denomination: 'MUKGRES'.

BACKGROUND OF THE INVENTION

The present invention relates to a new and distinct cultivar of *Aglaonema* plant, botanically known as *Aglaonema hybrida* and hereinafter referred to by the name 'Mukgres'.

The new *Aglaonema* plant is the product of a controlled breeding program conducted by the Inventor in Chamrajpet, Bangalore, India. The objective of the breeding program is to create new full, dense and compact *Aglaonema* plants with good plant vigor, interesting and unique leaf shapes and variegation patterns, resistance to pathogens and pests and tolerance to low temperatures.

The new *Aglaonema* plant is the product of a cross-pollination conducted by the Inventor on Mar. 6, 2004 of a proprietary selection of *Aglaonema hybrida* identified as code number 2002-18, not patented, as the female, or seed, parent with *Aglaonema commutatum* var. *maculatum* 'Malay Lady Compact', not patented, as the male, or pollen, parent. The new *Aglaonema* plant was discovered and selected by the Inventor in April, 2005 as a single plant from within the resultant progeny of the stated cross-pollination in a controlled environment in Tiruporur, Chennai, India.

Asexual reproduction of the new *Aglaonema* plant by cuttings and divisions in a controlled environment in Tiruporur, Chennai, India since August, 2005 has shown that the unique features of this new *Aglaonema* plant are stable and reproduced true to type in successive generations of asexual reproduction.

SUMMARY OF THE INVENTION

Plants of the new *Aglaonema* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mukgres'. These characteristics in combination distinguish 'Mukgres' as a new and distinct *Aglaonema* plant:

1. Upright and outwardly arching plant habit.
2. Freely clumping habit.
3. Vigorous growth habit.
4. Relatively short internodes giving a compact, dense and full plant form.
5. Lanceolate leaves with dark green-colored midveins, margins and irregular chevrons alternating with contrasting greyed green-colored irregular chevrons.
6. Dark green-colored petioles.
7. Relatively tolerant to low temperatures.

Plants of the new *Aglaonema* differ from plants of the female parent selection in the following characteristics:

1. Plants of the new *Aglaonema* are smaller, fuller and denser than plants of the female parent selection.
2. Plants of the new *Aglaonema* have smaller leaves than plants of the female parent selection.
3. Plants of the new *Aglaonema* and the female parent selection differ in leaf shape, coloration and variegation pattern.
4. Plants of the new *Aglaonema* are more low temperature tolerant than plants of the female parent selection.

Plants of the new *Aglaonema* differ from plants of the male parent, 'Malay Lady Compact', in the following characteristics:

1. Plants of the new *Aglaonema* are larger and denser than plants of 'Malay Lady Compact'.
2. Plants of the new *Aglaonema* have larger and flatter leaves than plants of 'Malay Lady Compact'.
3. Plants of the new *Aglaonema* and 'Malay Lady Compact' differ in leaf coloration and variegation pattern.
4. Plants of the new *Aglaonema* are more low temperature tolerant than plants of 'Malay Lady Compact'.

Plants of the new *Aglaonema* can be compared to plants of *Aglaonema hybrida* 'Maria', not patented. In side-by-side comparisons conducted in Chamrajpet, Bangalore, India, plants of the new *Aglaonema* differed from plants of 'Maria' in the following characteristics:

1. Plants of the new *Aglaonema* were larger and denser than plants of 'Maria'.
2. Plants of the new *Aglaonema* had larger, broader and flatter leaves than plants of 'Maria'.
3. Plants of the new *Aglaonema* and 'Maria' differed in leaf coloration.
4. Plants of the new *Aglaonema* were more low temperature tolerant than plants of 'Maria'.

Plants of the new *Aglaonema* can also be compared to plants of *Aglaonema hybrida* 'Mary Ann', disclosed in U.S. Plant Pat. No. 8,976. In side-by-side comparisons conducted in Chamrajpet, Bangalore, India, plants of the new *Aglaonema* differed from plants of 'Mary Ann' in the following characteristics:

1. Plants of the new *Aglaonema* were more uniform and denser than plants of 'Mary Ann'.
2. Plants of the new *Aglaonema* had smaller and flatter leaves than plants of 'Mary Ann'.
3. Plants of the new *Aglaonema* and 'Mary Ann' differed in leaf coloration.
4. Plants of the new *Aglaonema* were more low temperature tolerant than plants of 'Mary Ann'.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet comprises a side perspective view of a typical plant of 'Mukgres' grown in a container.

The photograph on the second sheet comprises a top perspective comparative view of typical plants of 'Mukgres' (left) and 'Maria' (right).

The photograph on the third sheet comprises a top perspective comparative view of typical plants of 'Mukgres' (left) and 'Mary Ann' (right).

DETAILED BOTANICAL DESCRIPTION

The aforementioned photographs and following observations and measurements describe plants grown in 25-cm containers in Miami, Fla. during the summer and autumn in a polypropylene-covered shadehouse. Plants were grown under environmental conditions and cultural practices which approximate those generally used in commercial *Aglaonema* production. During the production of the plants, day temperatures ranged from 27° C. to 37° C., night temperatures ranged from 15° C. to 26° C. and light levels averaged 1,500 foot-candles. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'Mukgres'.

Parentage:

*Female, or seed, parent.*—Proprietary selection of *Aglaonema hybrida* identified as code number 2002-18, not patented.

*Male, or pollen, parent.*—*Aglaonema commutatum* var. *maculatum* 'Malay Lady Compact', not patented.

Propagation:

*Type.*—By cuttings and divisions.

*Time to initiate roots, summer.*—About 21 to 28 days at 25° C. to 32° C.

*Time to initiate roots, winter.*—About 30 to 40 days at 12° C. to 25° C.

*Time to produce a rooted young plant, summer.*—About 30 to 35 days at 25° C. to 32° C.

*Time to produce a rooted young plant roots, winter.*—About 45 to 60 days at 12° C. to 25° C.

*Root description.*—Fleshy, medium in thickness; off-white in color.

*Rooting habit.*—Freely branching; profuse, high density.

Plant description:

*Plant and growth habit.*—Upright and outwardly arching plant habit; freely clumping habit; relatively short internodes giving a compact, full and dense habit; vigorous growth habit; developing leaves initially upright, then arching outwardly with development. Plant height, from soil level to top of leaf plane: About 45 cm.

*Plant diameter or spread.*—About 68 cm.

*Stem description.*—Clumping habit: Plants of the new *Aglaonema* are freely clumping with about 16 clumps developing per container. Aspect: Mostly upright. Strength: Strong; somewhat flexible. Diameter, at the base: About 1.7 cm. Internode length, at the base: About 1.4 cm. Color: Close to 147A. Cataphylls: None observed.

Foliage description:

*Arrangement.*—Alternate to whorled; simple.

*Length.*—About 25 cm.

*Width.*—About 7 cm.

*Shape.*—Lanceolate.

*Apex.*—Acuminate; straight.

*Base.*—Obtuse.

*Margin.*—Entire; very slightly undulate.

*Texture, upper and lower surfaces.*—Smooth, glabrous.

*Venation pattern.*—Pinnate.

*Color.*—Developing leaves, upper surface: Midvein, margins and irregular chevrons, closest to more green than 137A; alternating irregular chevrons, closest to 146C, 147C and/or 148C; lateral venation, same as leaf coloration. Developing leaves, lower surface: Closest to 146B; venation, close to 146B. Fully expanded leaves, upper surface: Midvein, margins and irregular chevrons, darker green than 147A; alternating irregular chevrons, closest to 191A and 191B; lateral venation, same as leaf coloration. Fully expanded leaves, lower surface: Closest to N137B; venation, close to N137B.

*Petiole.*—Aspect: Mostly erect, outwardly arching with development. Length: About 15 cm. Diameter, distal: About 5 mm. Diameter, proximal, flattened: About 2 cm. Strength: Strong; flexible. Color, distal: Close to 147A. Color, proximal: Close to 147B. Wing length: About 12 cm. Wing diameter, base: About 4 mm. Wing color, inner and outer surfaces: Close to 147A; area adjacent to stem, close to 157A to 157C.

Inflorescence description: Inflorescence development has not been observed on plants of the new *Aglaonema*.

Disease & pest resistance: Plants of the new *Aglaonema* have not been observed to be resistant to pathogens or pests common to *Aglaonema*.

Temperature tolerance: Plants of the new *Aglaonema* have been observed to be relatively low temperature tolerant and to tolerate temperatures ranging from about 15° C. to about 40° C.

It is claimed:

1. A new and distinct *Aglaonema* plant named 'Mukgres' as illustrated and described.

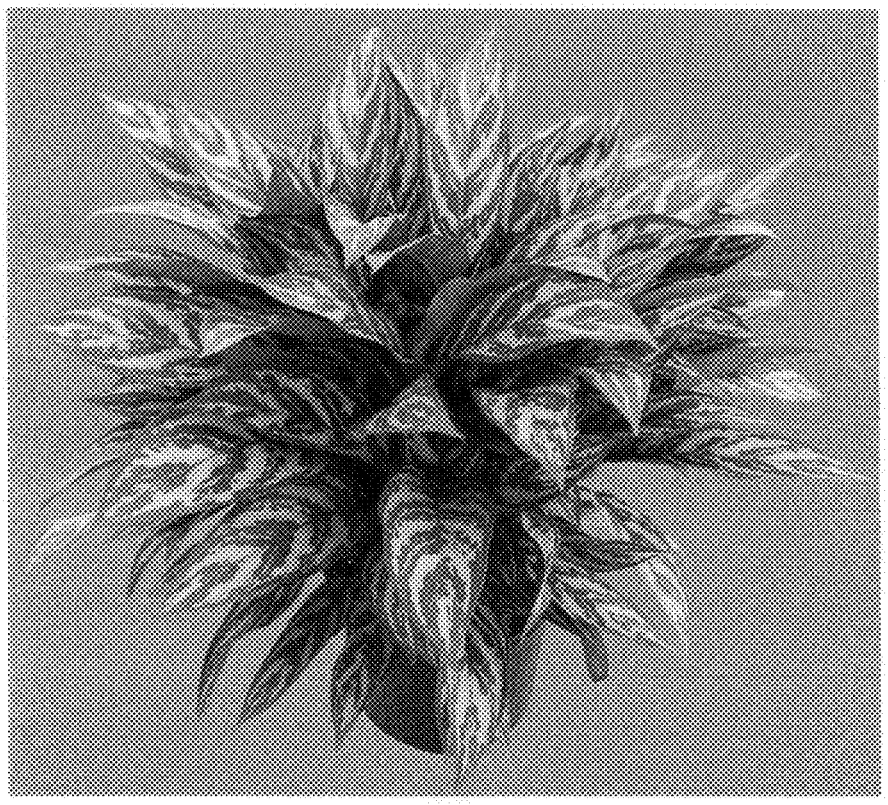

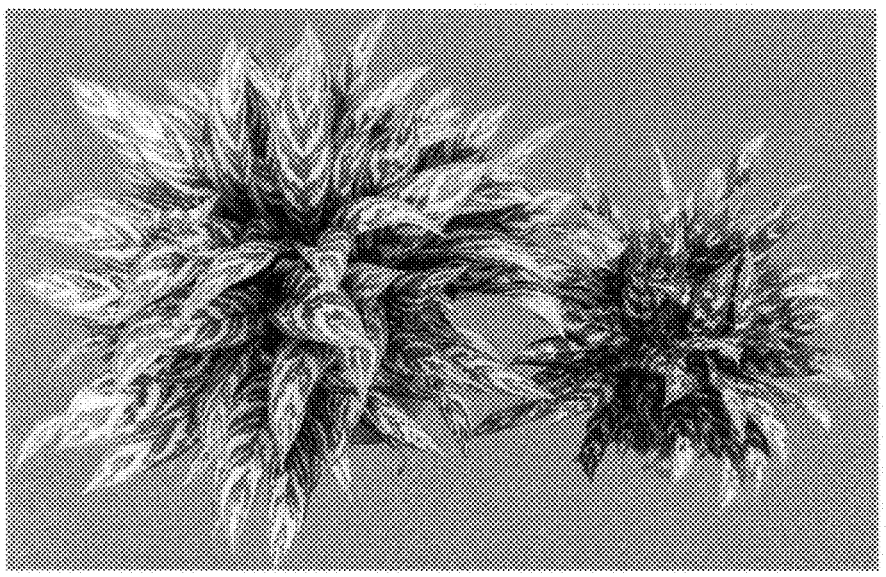

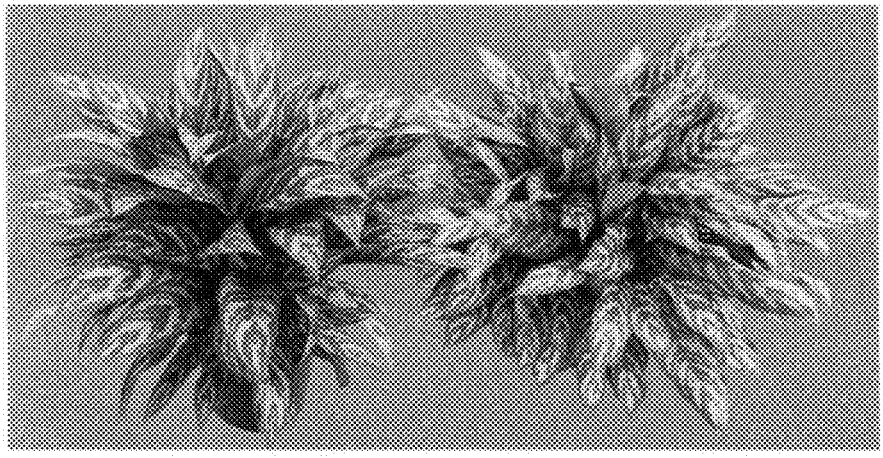

* * * * *